United States Patent
Shoji et al.

(10) Patent No.: US 6,589,410 B1
(45) Date of Patent: Jul. 8, 2003

(54) HYDROCARBON SENSOR

(75) Inventors: Rihito Shoji, Osaka (JP); Takashi Tamai, Osaka (JP); Noboru Taniguchi, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/601,892

(22) PCT Filed: Dec. 22, 1999

(86) PCT No.: PCT/JP99/07216
§ 371 (c)(1),
(2), (4) Date: Sep. 26, 2000

(87) PCT Pub. No.: WO00/39572
PCT Pub. Date: Jul. 6, 2000

(30) Foreign Application Priority Data

Dec. 24, 1998 (JP) .......................................... 10-367085
Jul. 5, 1999 (JP) .......................................... 11-190020

(51) Int. Cl.$^7$ .............................................. G01N 27/407
(52) U.S. Cl. ..................... 204/426; 204/408; 204/424; 204/425
(58) Field of Search ................. 204/421–429, 204/408

(56) References Cited

U.S. PATENT DOCUMENTS

| | | | |
|---|---|---|---|
| 3,597,345 A | * | 8/1971 | Hickam et al. |
| 4,505,807 A | * | 3/1985 | Yamada |
| 4,897,174 A | * | 1/1990 | Wang et al. |
| 4,961,835 A | * | 10/1990 | Kobayashi et al. |
| 5,108,577 A | * | 4/1992 | Mase et al. |
| 5,395,506 A | * | 3/1995 | Duce et al. |
| 5,474,665 A | * | 12/1995 | Friese et al. |
| 5,935,398 A | * | 8/1999 | Taniguchi et al. |
| 6,007,688 A | * | 12/1999 | Kojima et al. |
| 6,007,697 A | * | 12/1999 | Yagi et al. |

FOREIGN PATENT DOCUMENTS

| | | |
|---|---|---|
| EP | 772042 | 5/1997 |
| JP | 4-89562 | 3/1992 |
| JP | 7-248307 | 9/1995 |
| JP | 9-127055 | 5/1997 |
| JP | 6-347441 | 12/1997 |
| JP | 9-318592 | 12/1997 |

OTHER PUBLICATIONS

Gatewood, "Thermal Stresses", (1957), pp. 138–140.*

* cited by examiner

Primary Examiner—T. Tung
(74) Attorney, Agent, or Firm—McDermott, Will & Emery

(57) ABSTRACT

The invention presents a hydrocarbon sensor excellent in yield and high in detection precision. To achieve the object, the invention includes a solid electrolyte layer (1) contained barium-cerium oxide, a pair of electrodes, cathode (2) and anode (3), provided on the solid electrolyte layer (1), a ceramic substrate (4) having a coefficient of thermal expansion nearly same as that of the solid electrolyte layer (1), and a heater (7) provided on the ceramic substrate (4), in which the solid electrolyte layer (1) and ceramic substrate (4) are bonded to each other.

20 Claims, 12 Drawing Sheets

HYDROCARBON SENSOR

TECHNICAL FIELD

The present invention relates to a hydrocarbon sensor.

BACKGROUND ART

Hitherto, a hydrocarbon sensor using barium-cerium oxide as a solid electrolyte has been proposed (Japanese Laid-open Patent No. 9-127055).

A schematic structure of this hydrocarbon sensor is shown in FIG. 12. Reference numeral 101 is a solid electrolyte layer composed of barium-cerium oxide, and a cathode 102 and an anode 103 are formed on its surface by thick film printing process. On the solid electrolyte layer 101, a ceramic substrate 104 made of forsterrite is adhered and fixed with an adhesive of inorganic material (inorganic adhesive) 108. A heater 109 is formed on the surface of the ceramic substrate 104 by a thick film printing process. In part of the adhesion layer adhered by the inorganic adhesive 108, a diffusion rate-determining hole 111 (area indicated by dotted line in FIG. 12) for introducing hydrocarbon gas (HC) is provided.

The operation of this hydrocarbon sensor is explained. As shown in FIG. 12, a constant voltage is applied to the cathode 102 and anode 103. An ammeter for detecting the output is provided in the circuit. The solid electrolyte layer 101 is heated by a heater 109 in order to activate. In this state, when the HC passes through the diffusion rate-determining hole 111 to reach the anode 103, the HC is decomposed, and protons conduct through the solid electrolyte layer 101. As a result, current I flows in the circuit. The magnitude of this current I increases in proportion to the amount of protons, that is, the concentration of the HC. Therefore, the HC concentration can be detected from the output of the ammeter.

The hydrocarbon sensor having such structure is capable of obtaining a linear output corresponding to the HC concentration, and is free from effect of oxygen if coexisting while the HC concentration is low. In other words, the hydrocarbon sensor excellent in gas selectivity is obtained.

However, when applying such hydrocarbon sensor in HC detection in automobile emission, the solid electrolyte layer 101 must be activated. Accordingly, when the current flows in the heater 109, the ceramic substrate 104 on which the heater 109 is formed is subject to a significant stress, and known that the yield is lowered. In this mechanism, the following reasons are considered.

1) The coefficient of thermal expansion of the ceramic substrate 104 (forsterrite) on which the heater 109 is formed is 11 to $11.5 \times 10^{-6}/°$ C., whereas the coefficient of thermal expansion of the solid electrolyte layer 101 is about $10 \times 10^{-6}/°$ C., and the difference of the two is more than $1 \times 10^{-6}/°$ C.

2) The HC in the emission is a reducing atmosphere, and the ceramic substrate 104 is exposed to it, and part of composition (MgO forsterrite) of the ceramic substrate 104 is reduced, and the strength is reduced.

3) The platinum paste of the thick film for forming the heater 109 is a porous and uneven composition, and the current flow is concentrated in this area, and the temperature becomes high locally.

4) The heater 109 is formed at one side of the ceramic substrate 104 only, and this formed side is an exposed structure, and when the current flows in the heater 109 is this state, a temperature difference occurs suddenly between the heater forming side and the back side (the adhesion side with the solid electrolyte layer), and a large stress occurs.

The conventional hydrocarbon sensor also has other problem, that is, when the hydrocarbon sensor is installed in the automobile emission, the emission temperature varies with the engine running state, and the temperature of the hydrocarbon sensor may vary as much as $620 \pm 30°$ C. That is, the temperature variation width is 60° C. The output current of the hydrocarbon sensor varies not only with the HC concentration, but also with the temperature, and such temperature variation may cause to lower the accuracy of hydrocarbon sensor. This is because the temperature regulation precision of the heater 109 is not sufficient.

SUMMARY OF THE INVENTION

The invention solves these problems, and it is hence an object thereof to present a hydrocarbon sensor excellent in yield and high in detection precision.

To solve the problems, the hydrocarbon sensor of the invention comprises a solid electrolyte layer composed of barium-cerium oxide, a pair of electrodes provided on the solid electrolyte layer, a ceramic substrate having a coefficient of thermal expansion nearly same as that of the solid electrolyte layer, and a heater provided on the ceramic substrate, in which the solid electrolyte layer and ceramic substrate are bonded to each other.

Further, at the heater forming side of the ceramic substrate, an auxiliary substrate having a coefficient of thermal expansion nearly same as that of the ceramic substrate is provided.

Further, the heater comprises control means for controlling on/off switching of the heater, comparing means for comparing the resistance value of the heater and the target resistance value of the heater being predetermined corresponding to the temperature, and judging means for suppressing the output from the control means depending on the signal from the comparing means.

In this constitution, the hydrocarbon sensor excellent in yield and high in detection precision is obtained.

BEST MODE FOR CARRYING OUT THE INVENTION

Embodiment 1

Figure 1:
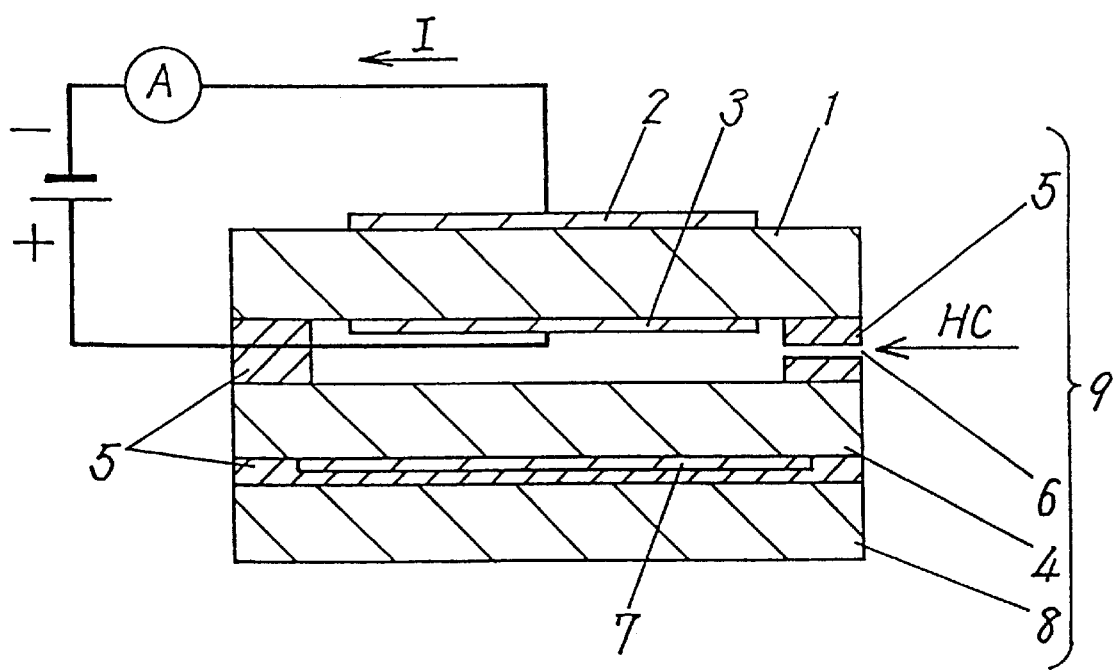
FIG. 1 is a schematic sectional view of a detection element in embodiment 1 of hydrocarbon sensor of the invention.
Figure 4:
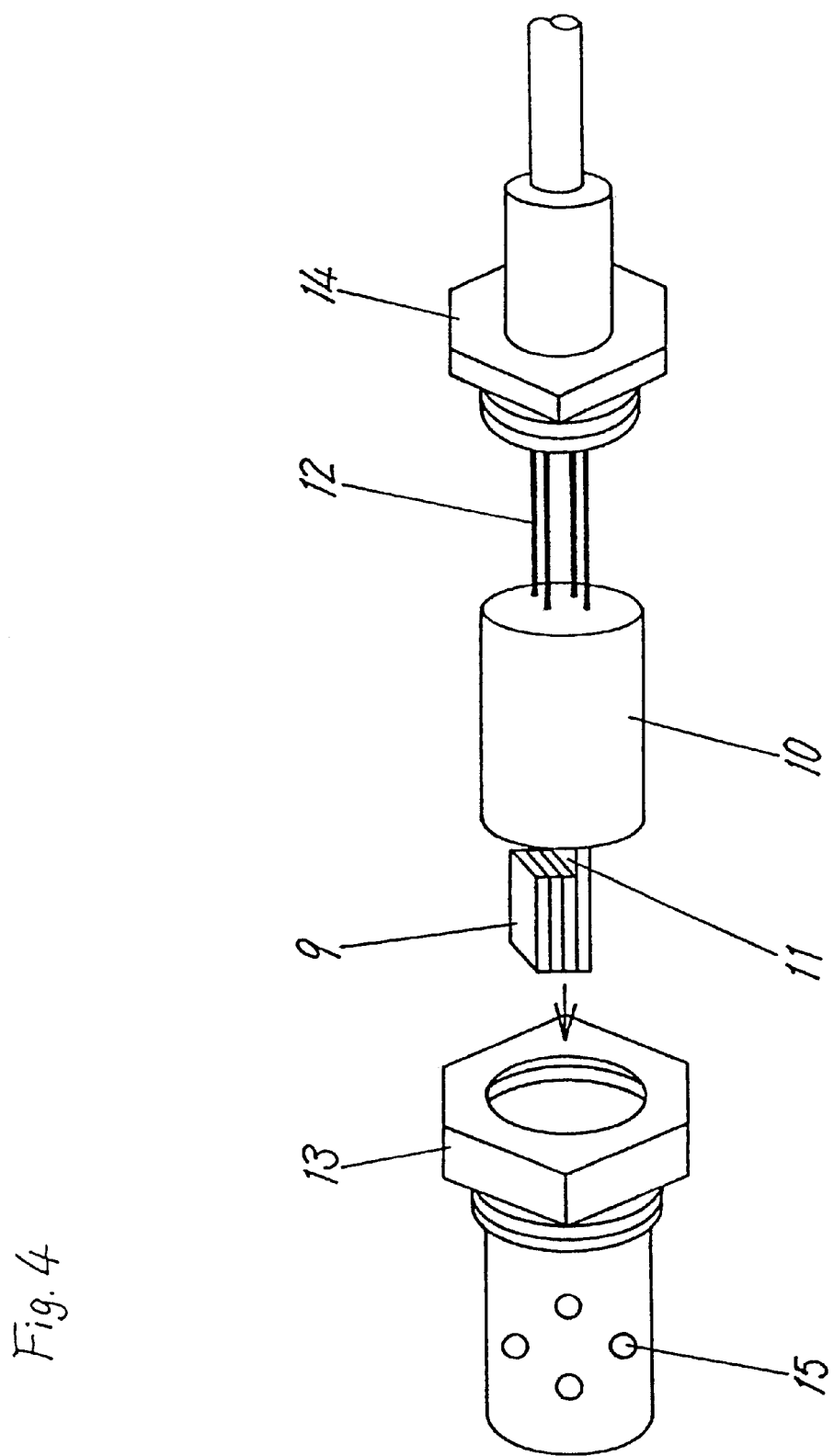
FIG. 4 is a perspective exploded view of a metallic case in embodiment 1.
Figure 5:
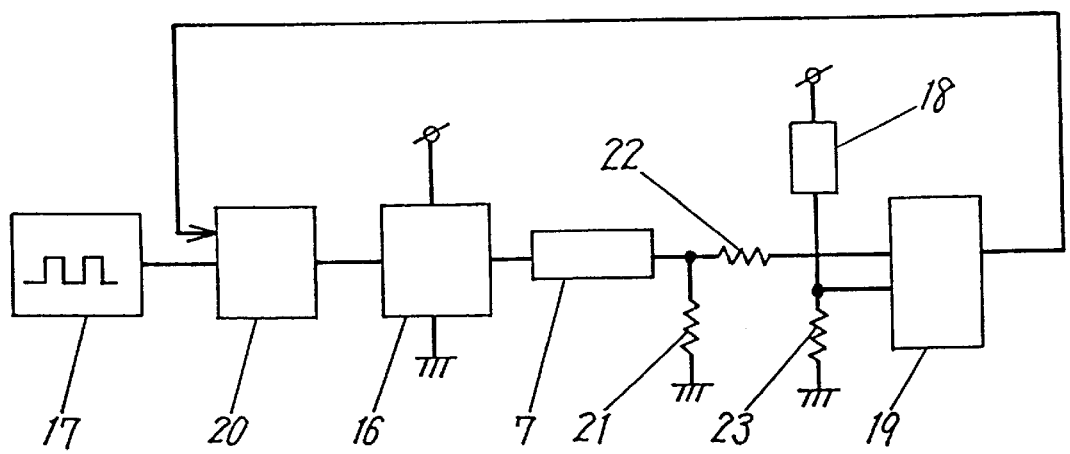
FIG. 5 is a block diagram explaining a drive circuit of the heater in embodiment 1.

FIG. 1 is a schematic sectional view of a detection element in embodiment 1 of hydrocarbon sensor of the invention. FIG. 2 is a heater pattern diagram. FIG. 3 is a schematic perspective view mainly explaining a flat part formed in a ceramic column for holding the detection element. FIG. 4 is a perspective exploded view of a metallic case for holding the ceramic column. FIG. 5 is a block diagram explaining a heater drive circuit.

Reference numeral 1 is a 10 mm square, 0.5 mm thick solid electrolyte layer composed of an oxide of barium, cerium and gadolinium, and a pair of electrodes composed of a cathode 2 and an anode 3 are formed by thick film printing and baking so as to contact with the surface thereof. An aluminum paste is used for forming the cathode 2, and a platinum paste, for forming the anode 3.

At the anode 3 side of the solid electrolyte layer 1, a ceramic substrate 4 made of partially stabilized zirconia nearly of the same size as the solid electrolyte layer 1 is bonded with an inorganic adhesive 5. Herein, glass paste is used as the inorganic adhesive 5, and after printing and baking to both solid electrolyte layer 1 and ceramic substrate 4, the both are joined together and baked again to be bonded. The coefficient of thermal expansion of the ceramic substrate 4 made of partially stabilized zirconia is $10 \times 10^{-6}/°$ C., which is similar to the coefficient of thermal expansion of the solid electrolyte layer 1 (about $10 \times 10^{-6}/°$ C.)

As shown in FIG. 1, a diffusion rate-determining hole 6 is formed by opening a part of the inorganic adhesive 5.

On the opposite side surface of the plane bonded with the solid electrolyte layer 1 of the ceramic substrate 4, platinum paste (product number TR709 of Tanaka Noble Metal) is printed, and by baking at 1100° C., a heater 7 is formed densely in a thick film. The pattern of the heater 7 is either folded type shown in FIG. 2(a) or concentric type shown in FIG. 2(b).

On the ceramic substrate 4 forming the heater 7, an auxiliary substrate 8 made of partially stabilized zirconia of nearly same as the ceramic substrate 4 is bonded by means of the inorganic adhesive 5. Therefore, the ceramic substrate 4 and auxiliary substrate 8 can be matched in the coefficient of thermal expansion. As the inorganic adhesive 5, since a silicone adhesive (for example, Ceramabond No. 685 of Alemco) is used, its coefficient of thermal expansion is $10.8 \times 10^{-6}/°$ C. Therefore, as compared with the coefficient of thermal expansion of the partially stabilized zirconia, the difference in coefficient of thermal expansion is $0.8 \times 10^{-6}/°$ C., and both are nearly equal.

Bonding is done in a condition of heating and curing for 2 hours at 371° C.

Figure 3A:
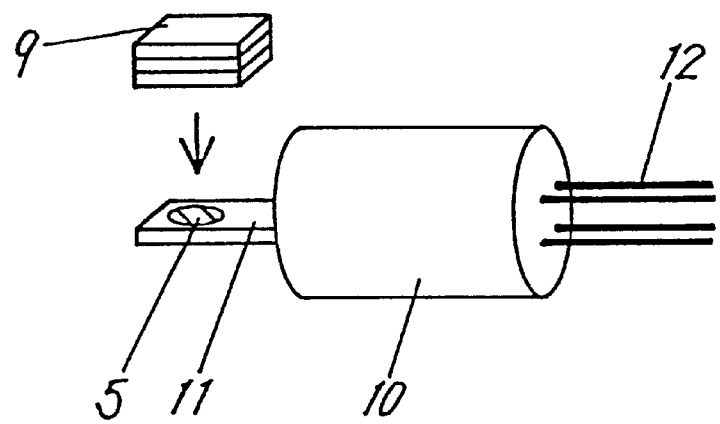
FIG. 3(a) is a schematic perspective view mainly explaining a flat part formed in a ceramic column in embodiment 1.
Figure 3B:
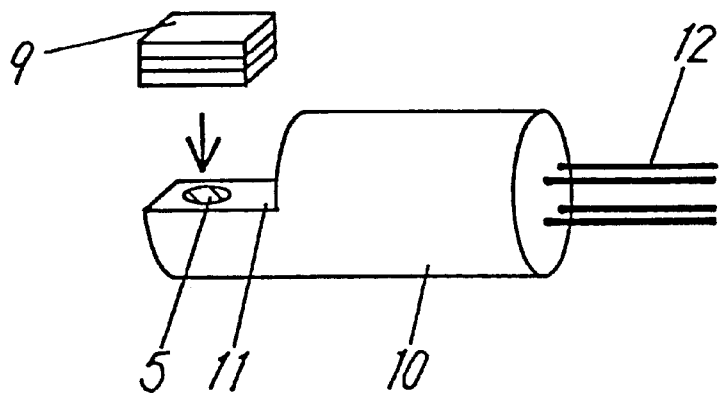
FIG. 3(b) is a schematic perspective view of the same.

Thus completed detection element 9 is fixed to a flat part 11 provided at one end of a ceramic column 10 by means of the inorganic adhesive 5 as shown in FIG. 3(a) or FIG. 3(b). The ceramic column 10 must be shaped as shown in FIG. 3(a) or FIG. 3(b). It is also required to form a through-hole in the ceramic column 10 in order to pass lead wires (described later) inside, and it is preferred to be made of a free-cutting material (for example, silica glass ceramic Macor, a tradename of Corning). The coefficient of thermal expansion of Macor is $9.4 \times 10^{-6}/°$ C., which is nearly same as the coefficient of thermal expansion of partially stabilized zirconia ($10 \times 10^{-6}/°$ C.) which is the material for the ceramic substrate 4. The inorganic adhesive 5 is Ceramabond same as above.

Inside of the ceramic column 10, lead wires 12 for sensor output and heater are passing, and connected electrically.

The ceramic column 10 is contained in a metallic case 13, and is fixed with a metallic lid 14. As shown in FIG. 4, the metallic case 13 had a ventilation hole 15 for passing emission, formed at a position corresponding to the detection element 9. The metallic case 13 and metallic lid 14 are both made of heat-resistant stainless steel in consideration of use in the automobile emission. In embodiment 1, SUS430 of JIS is used as the heat-resistant stainless steel, but SUS310 of JIS and other heat-resistant stainless steel can be also used.

The principle of detection of hydrocarbon sensor in embodiment 1 is basically same as in the prior art, and the construction and method for driving and controlling of the heater 7 are described in detail below.

In FIG. 5, reference numeral 16 is driving means for driving the heater 7, 17 is control means for on/off control, 18 is a reference resistance for defining a target resistance value, 19 is comparing means, 20 is judging means, and 21, 22, 23 are resistances.

Since the heater 7 is composed of a platinum resistor, the resistance-temperature coefficient is constant, and a proportional relation is established between the temperature and resistance value. Therefore, it is possible to select the reference resistance 18 corresponding to the target resistance value of the heater 7 preliminarily determined corresponding to the temperature (for example, 700° C.).

For example, when 12 V is supplied from the power source to the driving means 16 for driving the heater 7, until reaching the target temperature, the on/off repetition pulses (pulse frequency about 4 Hz) from the control means 17 are continuously given to the heater 7 through the AND circuit as the judging means 20.

When the temperature of the heater 7 reaches the target temperature, the resistance value of the heater 7 and the resistance value of the reference resistance 18 are matched, and the output from the-comparing means 19 becomes low level. Consequently, when this output is fed into the judging means 20, on/off repetition pulses are no longer given from the judging means 20 to the driving means 16, and heating of the heater 7 is stopped.

The hydrocarbon sensor having such structure was actually tested in automobile emission. As a result, the yield after passing current to the heater 7 reached 100% (10 times of testing).

It seems because the coefficient of thermal expansion of the solid electrolyte layer 1 and ceramic substrate 4 is matched, the auxiliary substrate 8 is installed, and its coefficient of thermal expansion is also matched, so that the stress of the heater 7 is extremely alleviated.

The following experiment was attempted to evaluate closely the temperature control function of the heater 7. To monitor the temperature of the detection element 9, a sample was prepared by adhering a thermocouple as temperature sensor to the solid electrolyte layer 1 by means of an organic adhesive, and temperature control was executed in a state of disposing it in the automobile emission. As a result, by varying the engine running situation, the conventional temperature variation width of 60° C. was suppressed to 8° C. only, by the temperature control as mentioned in the embodiment, and it has been verified that the temperature can be controlled at high accuracy.

It is also expected to control the temperature at high accuracy by disposing a temperature sensor in part of the detection element 9 for temperature control of the heater 7, always monitoring the temperature of the detection element 9, and controlling the current of the heater 7. As a result of actual study, however, no particular temperature control characteristic was obtained as compared with the structure of controlling by determining the temperature from the resistance value of the heater 7 itself. Therefore, it is not necessary to install a separate temperature sensor, in the temperature control method of the embodiment making use of the resistance value of the heater 7 itself, and it needs no additional lead wires, and the structure is simple, so that greater merits are obtained.

As the temperature control making use of the characteristic of the resistance value of the heater 7 itself mentioned in embodiment 1, many other structures for controlling may be considered (for example, feedback control).

Figure 2A:
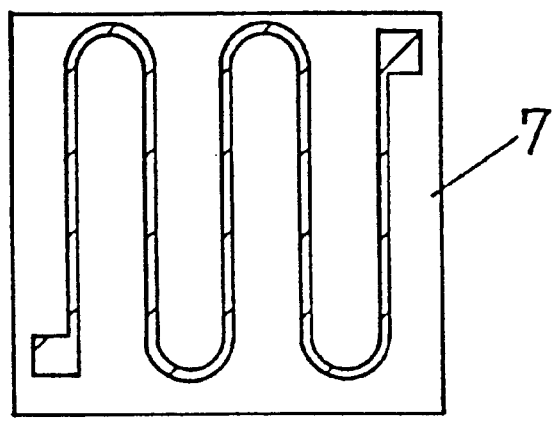
FIG. 2(a) is a pattern diagram of a heater in embodiment 1.
Figure 2B:
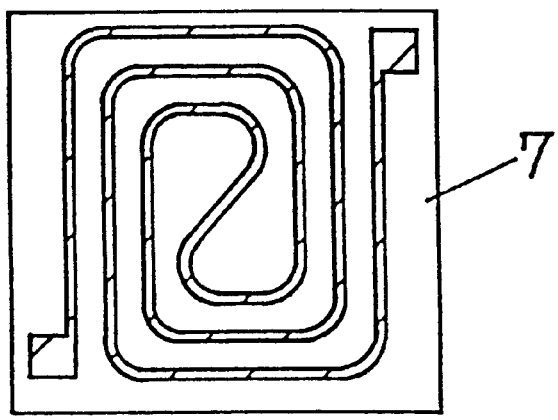
FIG. 2(b) is a pattern diagram of the same.

As the pattern of the heater 7, two modes shown in FIG. 2(a) and FIG. 2(b) are explained, and from the viewpoint of temperature control, an equally high precision is realized in either method. The difference between the two lies only in the difference in the resistance value of the heater when formed in the pattern of the same width, and hence either pattern may be selected so as to obtain the optimum resistance value in consideration of the required temperature, power consumption, etc. Similarly, the pattern width or interval of the heater 7, the number of folds, or the number of concentric circles may be properly selected so as to obtain the optimum resistance value in consideration of the required temperature, power consumption, etc., and it is limited to the patterns shown in FIG. 2(a) and FIG. 2(b).

As the shape of the ceramic column, two types are shown in FIG. 3(a) and FIG. 3(b), but either may be selected as far as the hydrocarbon sensor is formed. However, the flat part 11 shown in FIG. 3(a) is thin and is hence small in thermal capacity, and is longer in the temperature rise time when heating the heater 7, but in spite of these advantages, since it is thin, it is hard to form the flat part 11. In the case of the flat part 11 in FIG. 3(b), it is easy to process only by cutting a part of the column, but the thermal capacity of the flat part 11 is large, and it takes a longer temperature rise time. Therefore, FIG. 3(a) and FIG. 3(b) have mutually contradictory merits and demerits, and a proper shape and size may be selected in consideration of the required temperature rise time, processing cost, etc.

In embodiment 1, the auxiliary substrate 8 is used, but it is not absolutely necessary by comprehensively considering the required temperature, power consumption, and detection precision. This constitution, however, sufficiently conforms to the technical concept of the invention.

Specific material names, trade names and product numbers mentioned in embodiment 1 are examples for composing the hydrocarbon sensor, and the materials are not limited to these examples alone.

Hence, the hydrocarbon sensor excellent in yield and high in detection precision is realized.

Embodiment 2

Figure 6:
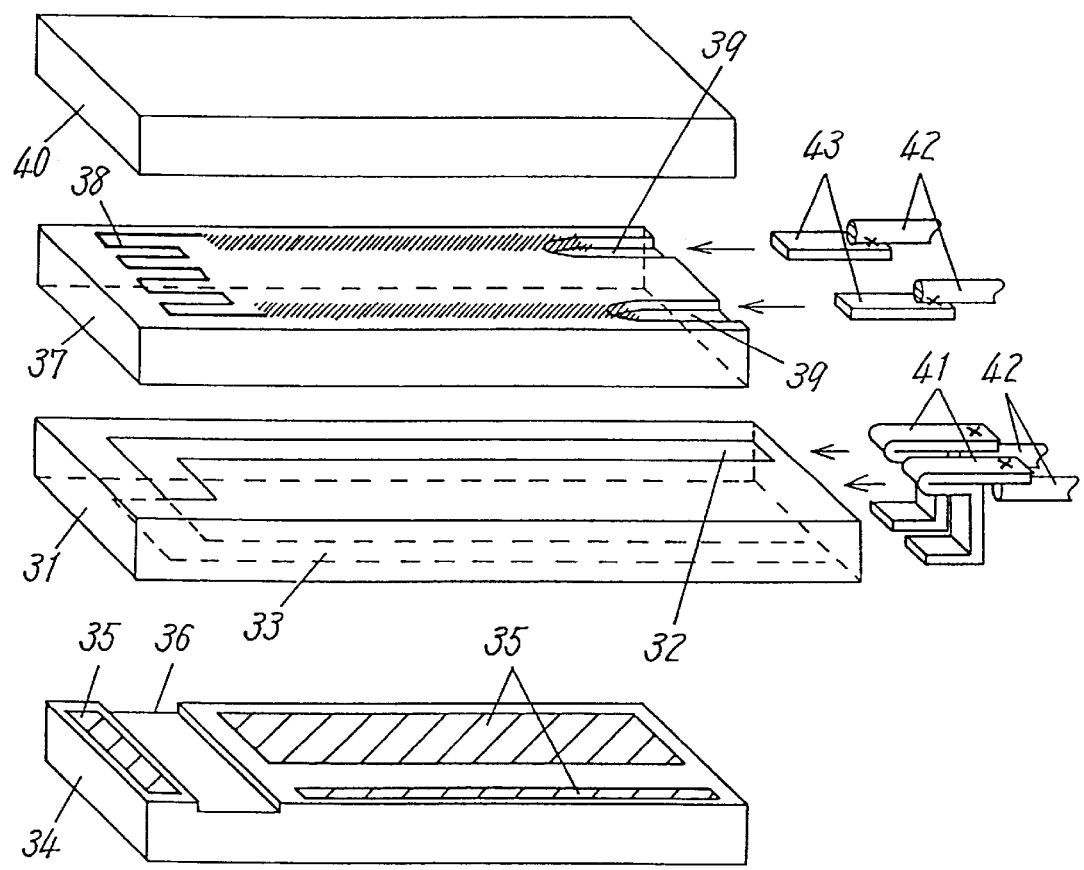
FIG. 6 is a perspective exploded view of a gas detector in embodiment 2 of hydrocarbon sensor of the invention.
Figure 7:
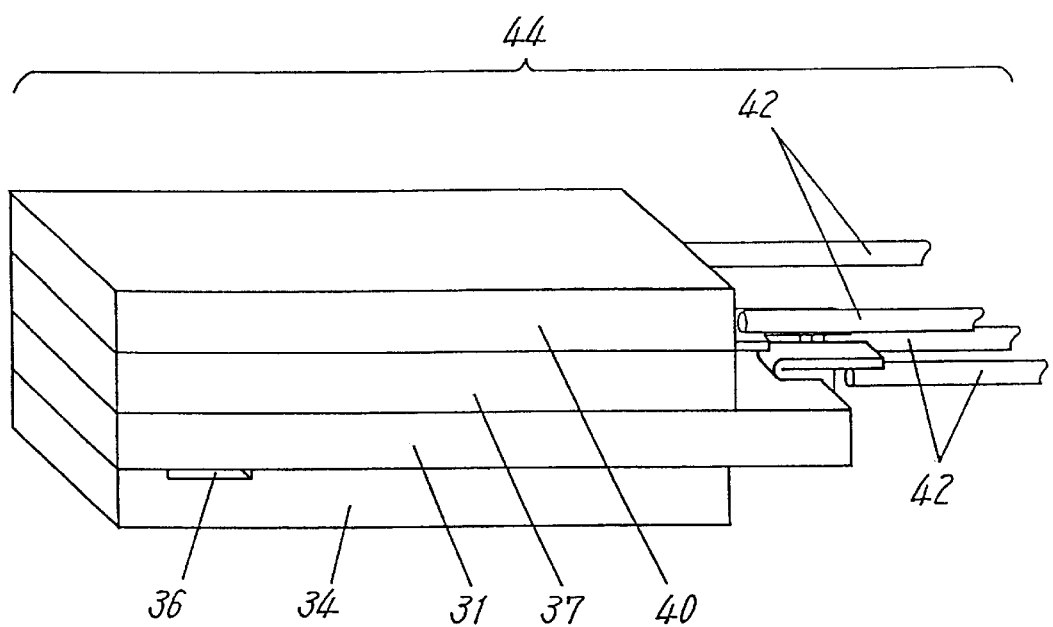
FIG. 7 is a perspective assembly diagram of the gas detector in embodiment 2.
Figure 8:
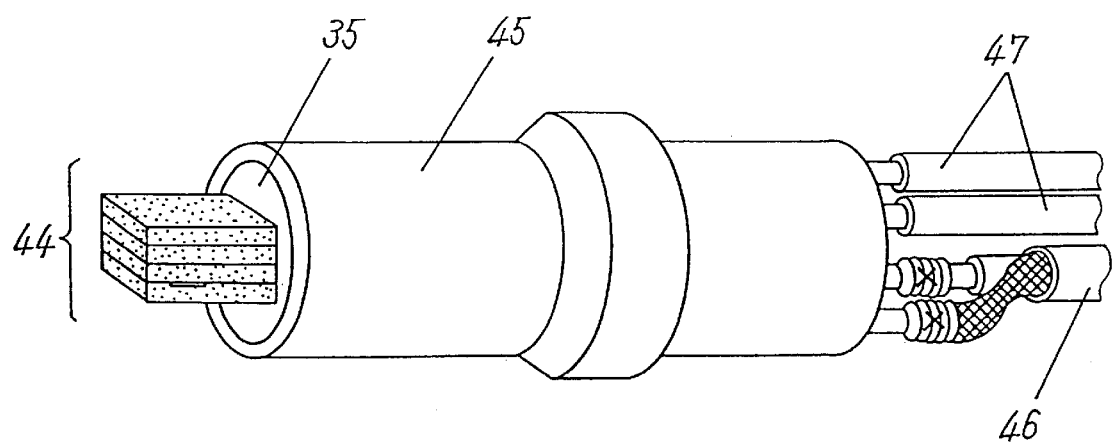
FIG. 8 is a perspective view of a sensor support stand in embodiment 2.
Figure 9:
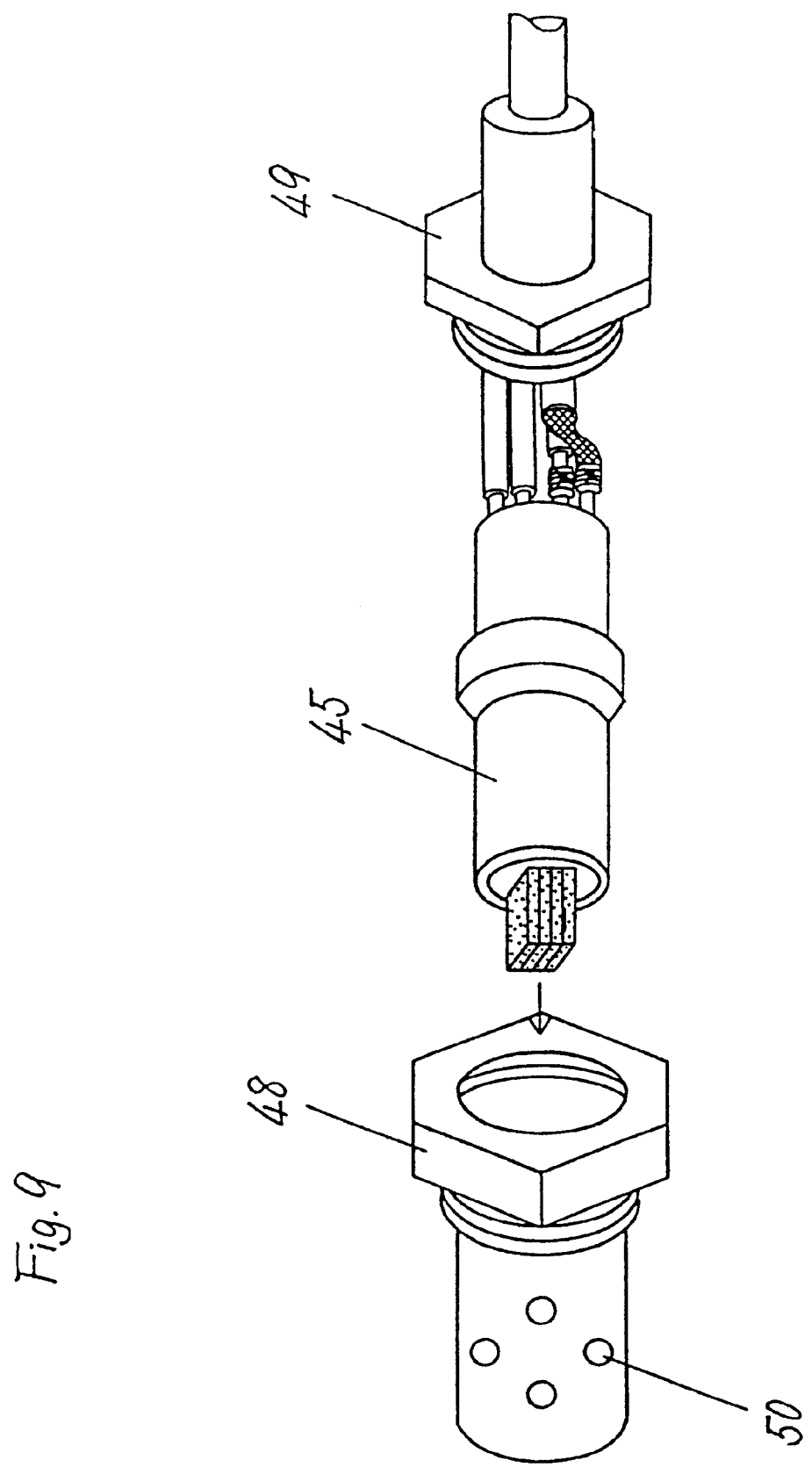
FIG. 9 is a perspective exploded view of a metallic case in embodiment 2.

FIG. 6 is a perspective exploded view of a gas detector in embodiment 2 of hydrocarbon sensor of the invention. FIG. 7 is a perspective assembly diagram of the gas detector. FIG. 8 is a perspective view of a sensor support stand fixing the gas detector. FIG. 9 is a perspective exploded view of a metallic case holding the sensor support stand.

Reference numeral 31 is a 5 mm wide, 20 mm long, 0.5 mm thick solid electrolyte substrate composed of an oxide of barium, cerium and gadolinium, and a pair of electrodes composed of a cathode 32 and an anode 33 are formed by thick film printing and baking so as to contact with the surface thereof. An aluminum paste is used for forming the cathode 32, and a platinum paste, for forming the anode 33. As shown in FIG. 6, the take-out electrode parts of the cathode 32 and anode 33 are integrally formed of a thick film paste. In these take-out electrode parts, a terminal 41 made of a 0.2 mm thick heat resistant stainless steel piece (for example, SUS430 of JIS) bent in a pi-shape is inserted into the solid electrolyte substrate 31.

The coefficient of thermal expansion of the SUS430 is about $12 \times 10^{-6}$/° C., which is nearly equal to the coefficient of thermal expansion of the solid electrolyte substrate 31 (about $10 \times 10^{-6}$/° C.), and the thermal stress on the solid electrolyte substrate 31 at high temperature is small, and heat resistance is excellent. In the inserting area, a strong adhesive thick film electrode paste (for example, product number TR1206 of Tanaka Noble Metal) is applied and baked, so that the terminal 41 and the solid electrolyte substrate 31 are electrically and mechanically connected. A copper compound lead wire 42 is electrically connected to the terminal 41 by laser welding (x-marked positions in FIG. 6).

At the anode 33 side of the solid electrolyte substrate 31, a 5 mm wide, 15 mm long, and 0.5 mm thick ceramic substrate 34 made of partially stabilized zirconia is bonded by means of an inorganic adhesive 35. Herein, as shown in FIG. 6, by forming a dent of 2 mm in width and 0.2 mm in depth at the leading end side of the ceramic substrate 34, a hydrocarbon gas lead-in port 36 is formed. As the inorganic adhesive 35, glass paste has been used hitherto, but in order to prevent clogging of the gas lead-in port 36 due to flow of glass when bonding, a high viscosity adhesive such as silica and alumina derivative is used. Bonding is done in a curing condition by heating for 2 hours at 371° C.

At the cathode 32 side of the solid electrolyte substrate 31, a 5 mm wide, 15 mm long, and 0.5 mm thick heater substrate 37 made of partially stabilized zirconia is bonded by means of an inorganic adhesive (not shown). On the surface of the opposite side of the side bonded with the solid electrolyte substrate 31 of the heater substrate 37, a platinum paste (for example, product number TR709 of Tanaka Noble Metal) is printed, and baked at 1100° C., and a heater 38 is formed. As shown in FIG. 6, in the take-out electrode part of the heater 38, a groove 39 is formed in a shape enough for inserting a 0.2 mm thick heater terminal 43 made of heat resistant stainless steel (SUS430 of JIS). After inserting the heater terminal 43 into the groove 39, by filling the gap with gold paste and baking, the heater substrate 37 and heater terminal 43 are electrically and mechanically connected. A copper compound lead wire 42 is electrically connected to the heater terminal 43 by laser welding (x-marked positions in FIG. 6).

On the heater 38 of the heater substrate 37, an auxiliary substrate 40 made of partially stabilized zirconia of the same size as the heater substrate 37 is bonded by means of an inorganic adhesive (not shown).

A perspective assembly view of thus completed gas detector 44 is shown in FIG. 7. The gas detector 44 is fixed by inserting a part not including the gas lead-in port into a sensor support stand 45 as shown in FIG. 8, and filling the gap between the two with an inorganic adhesive 35. The sensor support stand 45 must be shaped as shown in FIG. 8, and it is preferred to be made of a free-cutting heat resistant material (for example, silica glass ceramic Macor, a tradename of Corning).

The exposed part of the gas detector 44 including the solid electrolyte substrate 31 is covered with a coating material. It is enough to coat the exposed part of the solid electrolyte substrate 31 only, but the coating job efficiency is poor if limited to the solid electrolyte substrate 31, and the entire exposed parts including the solid electrolyte substrate 31 are coated in embodiment 2. As the coating material, in order to prevent peeling or dropping, it is preferred to use a heat resistant material having a same coefficient of thermal expansion as the solid electrolyte substrate 31, and the inorganic adhesive is applied and cured in this embodiment. Herein, the coefficient of thermal expansion of the inorganic adhesive is $10.8 \times 10^{-6}/°$ C., which is nearly same as the coefficient of thermal expansion of the solid electrolyte substrate 31 (about $10 \times 10^{-6}/°$ C).

A coaxial cable 46 is connected to two lead wires connected to the cathode 32 and anode 33 of the solid electrolyte substrate 31. The both are mutually twisted, and connected by applying laser welding of excellent heat resistance and secure electric connection to the parts (x-marked positions in FIG. 8). The laser welding zone is covered with a heat shrink tube (not shown) of high heat resistance (such as Teflon) so as hot to be shorted. The two lead wires leading to the heater 38 are also covered with a material 47 of high heat resistance (such as Teflon).

As shown in FIG. 9, the sensor support stand 45 is put in a metallic case 48, and fixed with a metallic lid 49. The metallic case 48 has a vent hole 50 for passing emission at a position corresponding to the gas detector 44. The metallic case 48 and metallic lid 49 are both made of heat resistant stainless steel (for example, SUS430 of JIS) in consideration of use in the automobile emission.

The hydrocarbon sensor having such structure was actually tested in automobile emission. As a result, no small sensor output was noted, and the element yield was remarkably improved. This is considered because the gas lead-in port 36 is formed by the dent in the ceramic substrate 34, and the solid electrolyte substrate 31 and ceramic substrate 34 are bonded with the inorganic adhesive 35 which does not flow at the time of curing, so that the gas lead-in port 36 is formed securely without being plugged.

Also there was no failure of sensor output due to engine vibration. This is because of the structure completely free from thin and fragile platinum tale-out wires which have been used in the prior art. Moreover, since the sensor output signal is detected by using copper compound lead wire and coaxial cable, engine noise is also reduced.

Embodiment 3

Figure 10:
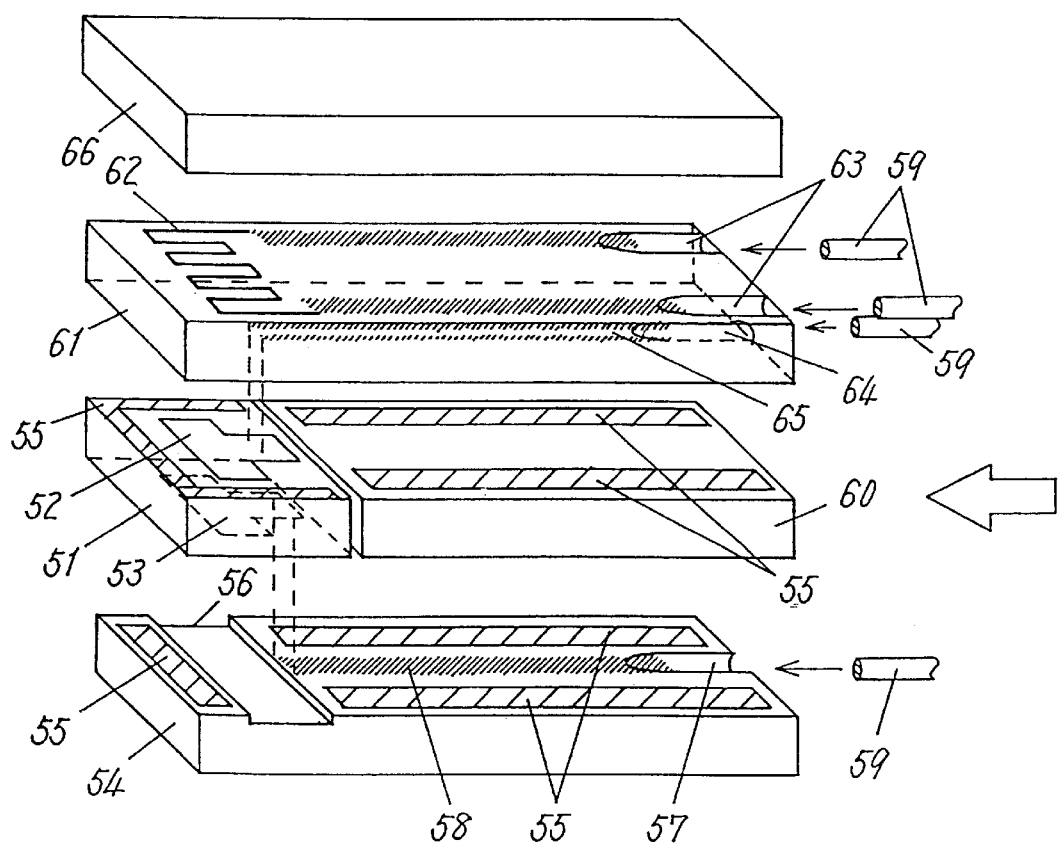
FIG. 10 is a perspective exploded view of a gas detector in embodiment 3 of hydrocarbon sensor of the invention.
Figure 11:
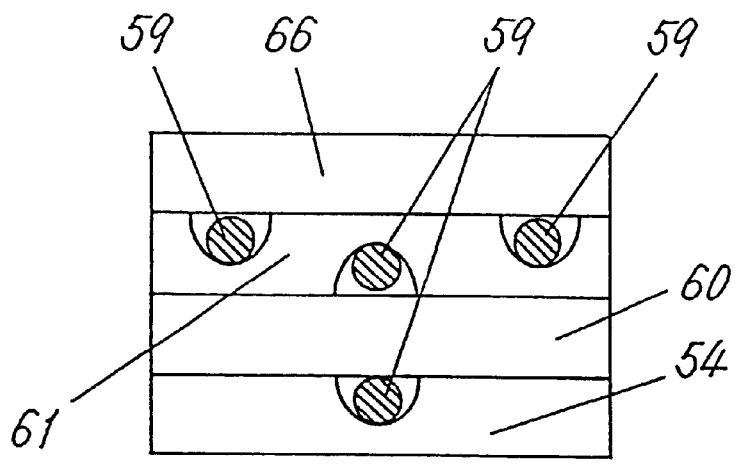
FIG. 11 is a front view of the gas detector in embodiment 3 as seen from the lead wire take-out side.
Figure 12:
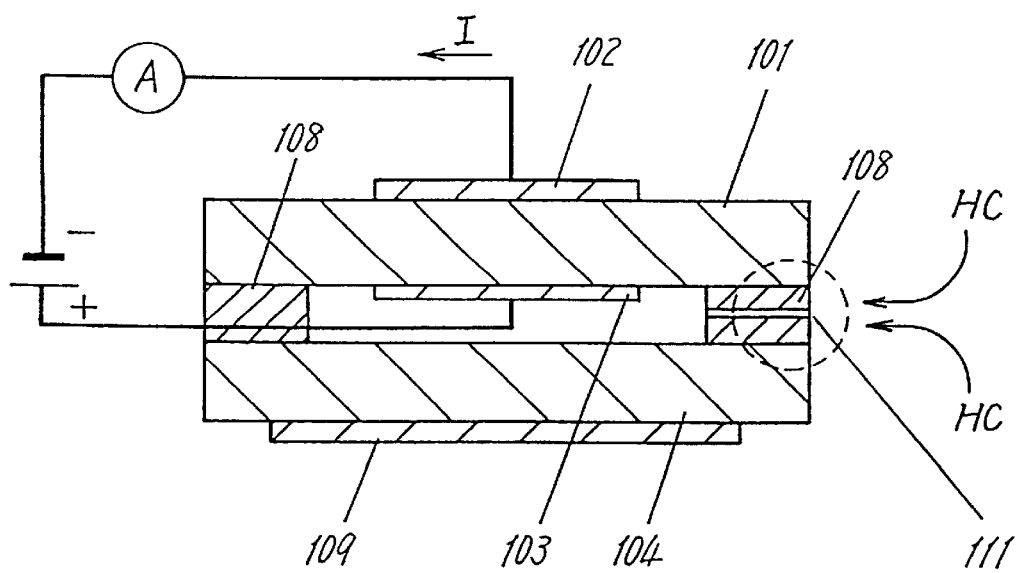
FIG. 12 is a schematic sectional view of a detecting element of a conventional hydrocarbon sensor.

FIG. 10 is a perspective exploded view of a gas detector in embodiment 3 of hydrocarbon sensor of the invention. FIG. 11 is a front view of the gas detector as seen from the lead wire take-out side.

Reference numeral 51 is a 5 mm wide, 5 mm long, 0.5 mm thick solid electrolyte substrate composed of an oxide of barium, cerium and gadolinium as a proton conductive oxide, and a pair of electrodes composed of a cathode 52 and an anode 53 are formed by thick film printing and baking so as to contact with the surface thereof. An aluminum paste is used for forming the cathode 52, and a platinum paste, for forming the anode 53.

At the anode 53 side of the solid electrolyte substrate 51, a 5 mm wide, 15 mm long, and 0.5 mm thick ceramic substrate 54 made of partially stabilized zirconia is bonded by means of an inorganic adhesive 55 same as used in embodiment 2. Herein, as shown in FIG. 10, by forming a dent of 2 mm in width and 0.2 mm in depth at the solid electrolyte substrate 51 bonded side of the ceramic substrate 54, a gas lead-in port 56 is formed. At the opposite side of the gas lead-in port 56, a semicircular anode dent 57 of 0.3 mm in radius is provided as shown in FIG. 10.

Herein, the length of the solid electrolyte substrate 51 is 5 mm, being longer than the width of 2 mm of the gas lead-in port 56 and shorter than the length of 15 mm of the ceramic substrate 54, but not limited to this, it is enough is far as the solid electrolyte substrate 51 covers the gas lead-in port 56 and has a portion joining with the ceramic substrate 54.

The anode dent 57 is filled with an anode conductive paste 58 (for example, product number TR1206 of Tanaka Noble Metal) so as to overlap with part of the dent at one end by thick film printing. Other end of the anode conductive paste 58 overlaps with part of the anode 53 when the ceramic substrate 54 and solid electrolytic substrate 51 are bonded as indicated by dotted line in FIG. 10, so as to be connected electrically. In the anode dent 57, moreover, a copper compound lead wire 59 of 0.3 mm in diameter is buried. The gap between the anode dent 57 and lead wire 59 is filled with a strong adhesive thick film conductive paste (for example, product number TR1206 of Tanaka Noble Metal), and baked, so that the anode conductive paste 58 and lead wire 59 are electrically connected, while the ceramic substrate 54 and lead wire 59 are mechanically connected at the same time.

Since the solid electrolyte substrate 51 and ceramic substrate 54 are different in area, the size corresponding to the area difference of the two, that is, a spacer 60 made of partially stabilized zirconia of 5 mm in width, 10 mm in length, and 0.5 mm in thickness is bonded to the ceramic substrate 54 by means of an inorganic adhesive 55.

At the cathode 52 side of the solid electrolyte substrate 51 and the spacer 50, a heater substrate 61 made of partially stabilized zirconia of 5 mm in width, 15 mm in length, and 0.5 mm in thickness is bonded by means of an inorganic adhesive 55. On the surface of the opposite side of the side bonded with the solid electrolyte substrate 51 of the heater substrate 61, a platinum paste (for example, product number TR709 of Tanaka Noble Metal) is printed, and baked at 1100° C., and a heater 62 is formed.

The take-out electrode part of the heater 62 is, as shown in FIG. 10, formed by thick film printing so as to overlap with part of a heater dent 63 of the same shape as the anode dent 57. Same as in the anode dent 57, a copper compound lead wire 59 is buried in the heater dent 63 by filling the gap with a thick film conductive paste.

At the back side of the heater dent 63, a cathode dent 64 of the same shape as the anode dent 57 is provided. In the cathode dent 64, a cathode conductive paste 65 similar to the anode conductive paste 58 is formed. As a result, by bonding the solid electrolyte substrate 51 and heater substrate 61, the cathode 52 and cathode conductive paste 65 are electrically connected. Same as in the anode dent 57, in the cathode dent 64, a copper compound lead wire 59 is buried by filing the gap of the two with a thick film conductive paste.

On the heater 62 of the heater substrate 61, an auxiliary substrate 66 made of partially stabilized zirconia in the same size as the heater substrate 61 is bonded by means of an inorganic adhesive (not shown).

A front view of thus assembled gas detector as seen from the arrow direction in FIG. 10 is shown in FIG. 11. The four lead wires 59 ranging from the cathode and anode to the heater are arranged at mutually non-interfering positions as shown in FIG. 11. The gas detector is fixed on the sensor support stand same as in embodiment 2, and is put in a metallic case. Likewise, the exposed part of the gas detector from the sensor support stand is covered with a coating material, and a coaxial cable is connected to two lead wires connected to the cathode and anode of the solid electrolyte substrate by laser welding.

The hydrocarbon sensor having such structure was actually tested in automobile emission. As a result, same as in embodiment 2, the element yield was remarkably improved, and the durability to the engine vibration was enhanced. This is considered because the gas lead-in port 56 is not clogged and platinum wires are not used.

Moreover, in embodiment 3, the amount of material for the solid electrolyte substrate 51 is ¼ as compared with that in embodiment 2, and the cost of the solid electrolyte substrate 51 can be reduced substantially.

Specific names, tradenames and product numbers of the materials mentioned in embodiment 1, 2 and 3 are only examples for composing the hydrocarbon sensor, and the materials are not limited to them alone.

Thus, the hydrocarbon sensor excellent in yield and durability to vibration is realized.

Industrial Applicability

The invention comprises a solid electrolyte layer composed of barium-cerium oxide, a pair of electrodes provided on the solid electrolyte layer, a ceramic substrate having a coefficient of thermal expansion nearly same as that of the solid electrolyte layer, and a heater provided on the ceramic substrate, in which the solid electrolyte layer and ceramic substrate are bonded to each other, and therefore a hydrocarbon sensor of an excellent yield is obtained.

Further, the heater comprises control means for controlling on/off switching of the heater, comparing means for comparing the resistance value of the heater and the target resistance value of the heater being predetermined corresponding to the temperature, and judging means for suppressing the output from the control means depending on the signal from the comparing means, and therefore a hydrocarbon sensor high in detection precision is realized.

Moreover, the constitution comprises a solid electrolyte substrate of a slender shape made of a proton conductive oxide, a pair of thin film electrodes formed on the face and back sides of the solid electrolyte substrate, a slender ceramic substrate having a hydrocarbon gas lead-in port on the surface of one electrode, and, a heater substrate of slender ceramics having a heater provided on the surface of other electrode, in which a part not including the hydrocarbon gas lead-in port of a gas detector obtained by integrally bonding the solid electrolyte substrate between the ceramic substrate and the heater substrate is inserted and fixed in a sensor support stand, and therefore a hydrocarbon sensor of excellent yield and excellent durability to vibration is obtained.

What is claimed is:

1. A hydrocarbon sensor comprising:
   a solid electrolyte plate containing barium-cerium oxide,
   a pair of electrodes provided on said solid electrolyte plate,
   a ceramic substrate having a coefficient of thermal expansion nearly the same as that of said solid electrolyte plate, wherein said ceramic substrate comprises partially stabilized zirconia,
   a heater provided on said ceramic substrate, and
   an auxiliary substrate disposed on a face of said ceramic substrate where said heater is provided, and
   wherein said solid electrolyte plate and said ceramic substrate are directly bonded to each other and the coefficient of thermal expansion of said ceramic substrate is nearly the same as that of said auxiliary substrate.

2. The hydrocarbon sensor of claim 1, wherein said heater is densely formed by a thick film forming process by using a platinum paste.

3. The hydrocarbon sensor of claim 1, wherein said ceramic substrate and said auxiliary substrate are bonded by means of an adhesive made of an inorganic material.

4. The hydrocarbon sensor of claim 3, wherein said adhesive has a coefficient of thermal expansion nearly the same as that of said ceramic substrate and said auxiliary substrate.

5. The hydrocarbon sensor of claims 1, further comprising
   driving means connected to said heater,
   control means for controlling on/off switching of said heater,
   comparing means for comparing the resistance value of said heater and the target resistance value of said heater being predetermined corresponding to the temperature, and
   judging means for suppressing the output from said control means depending on the signal from said comparing means.

6. The hydrocarbon sensor of claim 1, wherein said solid electrolyte plate, said ceramic substrate and said auxiliary substrate form a detection element, and said detection element is fixed to a flat part provided at one end of a ceramic column by means of an adhesive made of an inorganic material, and accommodated in a metallic case.

7. The hydrocarbon sensor of claim 6, wherein the coefficient of thermal expansion of said ceramic column is nearly equal to the coefficient of thermal expansion of said ceramic substrate or said auxiliary substrate.

8. The hydrocarbon sensor of claim 6, wherein the coefficient of thermal expansion of said adhesive is nearly equal to the coefficient of thermal expansion of said ceramic substrate.

9. The hydrocarbon sensor of claim 6, wherein said metallic case is made of heat resistant stainless steel.

10. The hydrocarbon sensor of claim 1, wherein said auxiliary substrate is made of a partially stabilized zirconia.

11. A hydrocarbon sensor comprising:
    a solid electrolyte substrate of proton conductive oxide, said substrate containing barium-cerium oxide,
    a pair of thin film electrodes formed on a face and a back face of said solid electrolyte substrate,
    a ceramic substrate having a gas lead-in port on a surface of one of said pair of thin film electrodes, said ceramic substrate having a coefficient of thermal expansion nearly the same as that of said solid electrolyte substrate,
    a heater substrate provided with a heater, said heater substrate directly bonded to a face of said solid electrolyte substrate where another one of said pair of thin film electrodes is formed, and having a coefficient of thermal expansion nearly the same as that of said solid electrolyte substrate, an auxiliary substrate disposed on a face of said heater substrate where said heater is provided, and a sensor support covering said solid electrolyte substrate, said ceramic substrate, said heater substrate and said auxiliary substrate, said sensor support not covering said gas lead-in port.

12. The hydrocarbon sensor of claim 11, wherein said solid electrolyte substrate is longer than the width of said gas lead-in port, and shorter than the length of said ceramic substrate, and said solid electrolyte substrate and a spacer are disposed and bonded between said ceramic substrate and said heater substrate.

13. The hydrocarbon sensor of claim 12, wherein said spacer has a coefficient of thermal expansion nearly the same as that of said solid electrolytic substrate.

14. The hydrocarbon sensor of claim 11, wherein take-out electrodes on said solid electrolyte substrate and take-out electrodes on said heater substrate are formed of a thick film paste, and a part of a terminal connected to each of said take-out electrodes is inserted into at least one of a part of said solid electrolyte substrate, said ceramic substrate and said heater substrate, and is bonded with a thick film paste.

15. The hydrocarbon sensor of claim 14, wherein said terminal is formed of heat resistant stainless steel, and is connected with a lead wire mainly composed of copper.

16. The hydrocarbon sensor of claim 15, wherein two lead wires connected to the take-out electrodes of said solid electrolyte substrate are connected to a coaxial cable.

17. The hydrocarbon sensor of claim 16, wherein said terminal and lead wires, and said lead wires and said coaxial cable are electrically connected by laser welding.

18. The hydrocarbon sensor of claim 11, wherein a part of said solid electrolyte substrate not covered with said sensor support is covered with a coating material made of an inorganic material.

19. The hydrocarbon sensor of claim 18, wherein said coating material has a coefficient of thermal expansion nearly same as that of said solid electrolyte substrate.

20. The hydrocarbon sensor of claim 11, wherein said sensor support, said solid electrolyte substrate, said ceramic substrate, said heater substrate and said auxiliary substrate are fixed by means of an inorganic adhesive.

* * * * *